US008586007B2

(12) United States Patent
Da Rocha et al.

(10) Patent No.: US 8,586,007 B2
(45) Date of Patent: Nov. 19, 2013

(54) CO-POLYMER STABILIZERS FOR HYDROFLUOROALKANE DISPERSIONS

(75) Inventors: Sandro R. P. Da Rocha, Troy, MI (US); Libo Wu, Detroit, MI (US)

(73) Assignee: Wayne State University, Detroit, MI (US)

( * ) Notice: Subject to any disclaimer, the term of this patent is extended or adjusted under 35 U.S.C. 154(b) by 466 days.

(21) Appl. No.: 12/738,826

(22) PCT Filed: Oct. 20, 2008

(86) PCT No.: PCT/US2008/080547
§ 371 (c)(1), (2), (4) Date: Sep. 8, 2010

(87) PCT Pub. No.: WO2009/052519
PCT Pub. Date: Apr. 23, 2009

(65) Prior Publication Data

US 2010/0322871 A1 Dec. 23, 2010

Related U.S. Application Data

(60) Provisional application No. 60/981,320, filed on Oct. 19, 2007.

(51) Int. Cl.

| | |
|---|---|
| *A61K 9/12* | (2006.01) |
| *A61K 47/30* | (2006.01) |
| *A61K 47/32* | (2006.01) |

(52) U.S. Cl.
USPC ........ 424/45; 514/772; 514/772.3; 514/772.6

(58) Field of Classification Search
USPC .................. 424/45; 514/772, 1, 772.6, 772.3
See application file for complete search history.

(56) References Cited

U.S. PATENT DOCUMENTS

| | | | | |
|---|---|---|---|---|
| 2,917,410 A * | 12/1959 | Vitalis | 442/148 |
| 6,126,919 A | 10/2000 | Stefely | 424/45 |
| 7,163,672 B2 * | 1/2007 | Buckton et al. | 424/45 |
| 2003/0194378 A1 * | 10/2003 | Rogueda | 424/45 |

FOREIGN PATENT DOCUMENTS

| | | |
|---|---|---|
| WO | WO/0203958 | 1/2002 |

OTHER PUBLICATIONS

"Montreal Protocol on Substance That Deplete The Ozone Layer," 261L.M . 1541, 1987.

Ashayer et al., "Investigation of The Molecular Interactions in a pMDI Formulation by Atomic Force Microscopy," *Colloids Surf. A* 21:533-543, 2004.

Begat et al., "The Cohesive-Adhesive Balances in Dry Powder Inhaler Formulations I: Direct Measurements by Atomic Force Microscopy," Pharm. Res. 21:1591-1597, 2004.

Bell and Newman, "The Rejuvenated Pressurised Metered Dose Inhaler," *Expert Opin. Drug Deliv.* 4:215-234, 2007.

Biggs and Proud, "Forces Between Silica Surfaces in Aqueous Solutions of a Weak Polyelectrolyte," *Langmuir* 13:7202-7210, 1997.

Braithwaite et al., "Interactions Between Poly(ethyleneoxide) Layers Adsorbed to Glass Surfaces Probed by Using a Modified AFM," *Langmuir* 12:4224-4237, 1996.

Bremmell et al., "Forces Between Surfaces in the Presence of a Cationic Polyelectrolyte and an Anionic Surfacant," *Colloids Surf. A* 155:1-10, 1999.

Bremmell et al., "Polyelectrolyte Adsorption at the Solid/Liquid Interface—Interaction Forces and Stability," *Colloids Surf. A* 139(2):199-211, 1998.

Butt et al., "Force Measurements With The Atomic Force Microscope: Technique, Interpretation and Applications," Surf. Sci. Rep. 59:1-152, 2005.

Byron and Patton, "Drug Delivery Via The Respiratory Tract," *J. Aerosol Med.* 7:49-75, 1994.

Byron et.al., "Some Aspects of Alternative Propellant Solvency," *Respir. Drug Deliv. IV* 231-242, 1994.

Courrier et al., "Pulmonary Drug Delivery System: Recent Developments and Prospects," Crit. Rev. Therapeu. Drug Carri. Syst. 19:425-498, 2002.

Dong and Feng, "Methoxy Poly(Ethylene Glycol)-Poly(Lactide) (MPEG-PLA) Nanoparticles for Controlled Delivery of Anticancer Drugs," *Biomaterials* 25:2843-2849, 2004.

Ducker and Senden, "Measurement of Forces in Liquids Using a Force Microscope," *Langmuir* 8:1831-1836, 1992.

Fink, "Metered-Dose Inhalers, Dry Powder Inhalers, and Transitions," *Respir. Care* 45:623-635, 2000.

Hagan et.al., "PLA-PEG Micelles—A Novel Drug Delivery System," *Proc. Intern. Symp. Control. Rel. Bioact. Mater.* 22:194-195, 1995.

Heller and Pugh, "Steric Stabilization of Colloidal Solutions by Adsorption of Flexible Macromolecules," *J. Polym. Sci.* 47:203-217, 1960.

Huang et al., "Methylated and Pegylated PLA—PCL—PLA Block Copolymers via the Chemical Modification of Di-Hydroxy PCL Combined with the Ring Opening Polymerization of Lactide," *Polym. Sci. A* 43:4196-4205, 2005.

Jalil, "Biodegradable Poly(Lactic Acid) Ahd Poly (Lactide-Coglycolide) Polymers in Sustained Drug Delivery," *Drug Dev. Ind. Pharm.* 16(16):2353-67, 1990.

Jones et al., "High-Pressure Aerosol Suspensions—A Novel Laser Diffraction Particle Sizing System for Hydrofluoroalkane Pressurised Metered Dose Inhalers," *Int. J. Pharm.* 302:154-165, 2005.

Jones et al., "Stabilisation of Deoxyribonuclease in Hydrofluoroalkanes Using Miscible Vinyl Polymers," J. Control. Rel. 115:1-8, 2006.

Luu et al., "Development of a Nanostructured DNA Delivery Scaffold via Electrospinning of PLGA and PLA-PEG Block Copolymers," *J. Control. Rel.* 89:341-353, 2003.

(Continued)

*Primary Examiner* — James H. Alstrum-Acevedo

(74) *Attorney, Agent, or Firm* — C. Rachal Winger; K&L Gates LLP

(57) ABSTRACT

The use of biodegradable and biocompatible lactide-based nonionic amphiphiles to stabilize a model drug (salbutamol base) dispersion in hydrofluoroalkane (HFA) propellant is disclosed. The results have industrial applicability to the development of HFA-based dispersion pressurized metered-dose inhaler formulations.

13 Claims, 5 Drawing Sheets

(56) References Cited

OTHER PUBLICATIONS

McDonald and Martin, "Transition to CFC-Free Metered Dose Inhalers -Into The New Millennium," *Int. J. Pharm.* 201:89-107, 2000.

McNamee et al., "Interaction Forces and Zeta Potentials of Cationic Polyelectrolyte Coated Silica Surfaces in Water and in Ethanol: Effects of Chain Length and Concentration of Perfluorinated Anionic Surfactants on Their Binding to the Surface," *Langmuir* 17:6220-6227, 2001.

Mohammadi-Rovshandeh et al., "Synthesis and Characterization of Novel ABA Triblock Copolymers From Llactide, Glycolide and PEG," *J. Appl. Polym. Sci.* 74:2004-7009, 1999.

Muir et al., "Interaction Forces Between a-Alumina Fibres With Coadsorbed Polyelectrolyte and Surfactant," *Langmuir* 17:4932-4939, 2001.

Okada et al., "Drug Delivery Using Biodegradable Microspheres," *J. Control. Rel.* 28:121-9, 1994.

Peguin et al., "Microscopic and Thermodynamic Properties of The HFA134a-Water Interface: Atomistic Computer Simulations and Tensiometry Under Pressure," *Langmuir* 22:8826-8830, 2006.

Peguin et al., "The Ester Group: How Hydrofluoroalkane-Philic Is It?" *Langmuir* 23:8291-8294, 2007.

Price et al., "The Influence of Relative Humidity on Particulate Interactions in Carrier-Based Dry Powder Inhaler Formulations," *Int. J. Pharm.* 246:47-59, 2002.

Ralston et al., "Atomic Force Microscopy and Direct Surface Force Measurements (IUPAC Technical Report)," *Pure Appl. Chem.* 77:2149-2170, 2005.

Ridder et al., "Surfactant Solubility and Aggregate Orientation in Hydrofluoroalkanes," Int. J. Pharm. 295:57-65, 2005.

Rogueda, "HPFP, A Model Propellant for pMDIs," *Drug Dev. Ind. Pharm.* 29:39-49, 2003.

Rogueda, "Novel Hydrofluoroalkane Suspension Formulations for Respiratory Drug Delivery," *Expert Opin. Drug Deliv.* 2:625-638, 2005.

Sakai et al., "Direct Force Measurements Between α-Alumina Surfaces With Adsorption of Anionic Surfactant/Polymer Mixtures," *Langmuir* 19:1203-1208, 2003.

Sakai, et al., "Interaction between Ionic Surfactants and Glass Surfaces With Covalently Attached Quaternary Ammonium Groups," Langmuir 17:4973-4979, 2001.

Sakai, et al., "Interaction Forces on α-Alumina Surfaces With Coadsorbed Anionic Surfactant and Nonionic Polymer," Langmuir 18:3993-3998, 2002.

Selvam et al., "Surfactant Design for The 1,1,1,2-Tetrafluoroethane-Water Interface: Ab Initio Calculations and in Situ High-Pressure Tensiometry," Langmuir 22:8675-8683, 2006.

Stefely et al., "Design and Utility of a Novel Class of Biocompatible Excipient for HFA-based MDIs," *Respir. Drug Delivery VII* 83-90, 2000.

Telko and Hickey, "Dry Powder Inhaler Formulation," *Respir. Care* 50:1209-27, 2005.

Traini et al., "Investigation Into the Influence of Polymeric Stabilizing Excipients on Inter-Particulate Forces in Pressurised Metered Dose Inhalers," Int. J. Pharm. 320:58-63, 2006.

Traini et al., "Surface Energy and Interparticle Forces Correlations in Model Pmdi Formulations," *Pharm. Res.* 22:816-825, 2005.

Tzou et al., "Drug From Selection in Albuterol-Containing Metered-Dose Inhaler Formulation and Its Impact on Chemical and Physical Stability," J. Pharm. Sci. 86:1352-1357, 1997.

Vervaet and Byron, "Drug-Surfactant-Propellant Interactions in HFA-Formulations," *Int. J. Pharm.* 186:13-30, 1999.

Vila et al., "PEG-PLA Nanoparticles As Carriers for Nasal Vaccine Delivery," *J. Aerosol Med.* 17:174-185, 2004.

Williams et al., "Application of Co-Grinding to Formulate a Model pMDI Suspension," *Eur. J. Pharm. Biopharm.* 48:131-140, 1999.

Wu and da Rocha, "Biocompatible and Biodegradable Copolymer Stabilizers for Hydrofluoroalkane Dispersions: A Colloidal Probe Microscopy Investigation," *Langmuir* 23(24):12104-12110, 2007.

Wu et al., "Core-shell particles for the Dispersion of Small Polar Drugs and Biomolecules in Hydrofluoroalkane Propellants," *Pharm. Res.* 25(2):289-301, 2008.

Wu et al., "Understanding Solvation in Hydrofluoroalkanes: Ab Initio Calculations and Chemical Force Microscopy," J. Phys. Chem. B. 111:8096-8104, 2007.

Young et al., "Investigation Into the Effect of Humidity on Drug-Drug Interactions Using The Atomic Force Microscope," *J. Pharm. Sci.* 92:815-822, 2003.

Young et al., "The Influence of Relative Humidity on The Cohesion Properties of Micronised Drugs Used in Inhalation Therapy," *J. Pharm. Sci.* 93:753-761, 2004.

Young et al., "Under Pressure: Predicting Pressurized Metered Dose Inhaler Interactions Using The Atomic Force Microscope," J. Colloid Interface Sci. 261:298-302, 2003.

Rutland and Senden, "Adsorption of The Poly(oxyethylene) Nonionic Surfactant C12E5 to Silica: A Study Using Atomic Force Microscopy," *Langmuir* 9:412-418, 1993.

\* cited by examiner

CO-POLYMER STABILIZERS FOR HYDROFLUOROALKANE DISPERSIONS

CROSS-REFERENCES TO RELATED APPLICATIONS

This application is a 371 national stage entry of International Patent Application No. PCT/US2008/080547 filed Oct. 20, 2008 which claims priority to U.S. Provisional Application No. 60/981,320 filed Oct. 19, 2007, the entire contents of each of which are incorporated by reference herein.

FIELD OF THE DISCLOSURE

Formulations and methods disclosed herein provide hydrofluoroalkane-based formulations for pressurized metered-dose inhalers comprising 1,1,1,2,3,3,3-heptafluoropropane and a lactide-based triblock copolymer of the formula poly(lactide)-poly(ethylene glycol)-poly(lactide): $LA_mEO_nLA_m$.

BACKGROUND OF THE DISCLOSURE

Pressurized metered dose inhalers (pMDIs) are the most common vehicles for the delivery of drugs to the lungs, accounting for approximately 80% of total prescribed aerosols. However, the development of pMDI-based formulations has been confronted with several challenges since the replacement of chlorofluorocarbons (CFCs) with the more environmentally friendly hydrofluoroalkane (HFA) propellants. In spite of the fact that the operation of pMDIs with HFAs is similar to those containing CFCs, previous formulations are generally not compatible due to differences in physicochemical properties between these two classes of fluids.

Surface active agents (surfactants) are generally required excipients in both solution and dispersion formulations for valve lubrication and to provide stability to dispersed drug crystals. One of the issues in reformulating pMDIs with HFAs is related to the fact that hydrocarbon-based surfactants used in FDA-approved CFC formulations (oleic acid, sorbitan trioleate, and lecithin) have extremely low solubility in the more polar semi-fluorinated propellants. Accordingly, cosolvents have been generally employed in HFA-based formulations in order to enhance surfactant solubility. However, the presence of cosolvents in pMDIs can affect the vapor pressure of the propellant—thus affecting the size of the aerosol. Cosolvents can also negatively impact the chemical and physical stability of the formulations.

CFC-based dispersions of salbutamol (base) have been extensively employed in the treatment of asthma. Oleic acid was typically used as a dispersing agent and as a valve lubricant in CFC-based pMDIs. However, oleic acid is not compatible with HFAs. While the solubility of oleic acid can be enhanced in the semifluorinated propellants upon the addition of ethanol, such an approach is not always suitable. This restriction is related to the fact that salbutamol has an appreciable solubility in ethanol, and the presence of the cosolvent decreases the chemical stability of the formulation. Therefore, the salt of salbutamol, salbutamol sulfate, which has low solubility in ethanol, is currently being used in HFA-based pMDI formulations.

The discussion above illustrates the challenges in reformulating pMDIs with HFA-based propellants. In light of such difficulties, the development of novel amphiphiles (chemical compounds having both hydrophilic and lipophilic properties) for HFA-based suspensions has been fairly limited. This can be attributed, at least in part, to challenges in obtaining United States Food & Drug Administration (FDA) approval for new excipients. On the other hand, difficulties associated with studying the colloidal/interfacial properties of such systems in situ, and a lack of a fundamental understanding of solvation forces in semifluorinated solvents, have also hindered the development of new amphiphiles for HFA suspensions.

Colloidal probe microscopy (CPM) is a powerful technique for the screening of surface-active agents for colloidal suspensions. CPM is an atomic force microscopy (AFM)-based technique where the force of interaction between a colloidal particle attached to an AFM tip and another particle/substrate of interest is measured with high resolution. CPM has been widely used to investigate the effect of surfactants and other polymers on the interaction forces between colloidal particles in aqueous phase as well as in nonaqueous media. CPM has also been used to characterize the cohesive/adhesive force between particles of relevance in the pharmaceutical industry. In the context of inhalation therapy, the CPM literature has focused primarily on dry powder formulations. CPM has also been applied to a few systems of relevance to pMDIs, including the study of the ability of poly(ethylene glycol) (PEG) and polyvinylpyrrolidone (PVP) to screen the cohesive forces of drug particles in 2H,3H perfluoropentane (HPFP), a mimicking solvent to propellant HFA, and the adhesive forces between drug particles and the walls of pMDI canisters.

SUMMARY OF THE DISCLOSURE

The present disclosure provides methods for screening excipients for hydrofluoroalkane-based pharmaceutical compositions. In one embodiment, at least one lactide-based amphiphile is used to screen the cohesive forces of a model drug. In another embodiment, the model drug is salbutamol base. In another embodiment, the lactide-based amphiphile is a lactide-based triblock copolymer of the formula poly(lactide)-poly(ethylene glycol)-poly(lactide): $LA_mEO_nLA_m$. In another embodiment, the pharmaceutical composition is a pressurized metered-dose inhaler formulation. In another embodiment, the pharmaceutical composition comprises propellant 1,1,1,2,3,3,3-heptafluoropropane.

DETAILED DESCRIPTION

The ability of novel nonionic amphiphiles to stabilize drug dispersions in HFAs was investigated. A salbutamol base was used as a model of an HFA-insoluble drug. The HFA-philic portion of the surfactant molecule was based on the biocompatible and biodegradable lactide (LA) moiety. Using ab initio calculations and chemical force microscopy, the HFA-philicity of the ester moiety was quantified and showed that LA is a promising surfactant tail candidate for HFA-based dispersion pMDIs. A series of triblock copolymers with general architecture $LA_n EO_m LA_n$ (where EO is ethylene oxide and the subscripts represent the average number of repeat units), and with varying hydrophilic-to-HFA-philic balance, were synthesized. The use of copolymers of LA and EO has not been explored in HFA-based pMDI formulations. CPM was used to probe the ability of these surfactants in screening the cohesive forces between drug particles in 2H,3H-perfluoropentane (HPFP), a mimicking solvent for HFAs. The CPM results obtained for the LA-based amphiphiles were compared and contrasted with those for ethanol-HPFP mixtures with or without lecithin (excipients in FDA-approved formulations), and those for an HPFP solution with a nonionic surfactant with the propylene oxide (PO) as the HFA-phile. The adhesion force (Fad) determined by CPM in the model propellant was correlated with the macroscopic physical stability from sedimentation rate experiments in HPFP and in the compressed propellant 1,1,1,2,3,3,3-heptafluoropropane (HFA227).

Materials and Methods

Materials. PEG600, -1000, and -2000 were purchased from Aldrich Chemicals Ltd. All PEGs were dried by azeotropic distillation with toluene to remove trace amounts of water before use. dl-Lactide was obtained from Frinton Laboratories, and it was recrystallized from ethyl acetate twice before use. Stannous octoate was purchased from Sigma. 2H,3H-Perfluoropentane (HPFP, 98%) was from SynQuest Labs and was purified by distillation over basic alumina. Pharma-grade 1,1,1,2,3,3,3-heptafluoropropane (HFA227) was a gift from Solvay. Salbutamol base (large crystals) was obtained from Spectrum Chemicals, Inc. Micronized salbutamol particles were obtained from a commercial CFC formulation (Armstrong Pharmaceuticals, Inc.). The particles were thoroughly washed with ethyl ether to remove oleic acid, an excipient present in the formulation. The purity of the obtained salbutamol particles was determined by reverse-phase HPLC (Beckman Coulter, Inc.) with a Synergi 4 Polar-RP column. No residual oleic acid or any other impurities were detected after the washing procedure. Oleic acid was supplied by Aldrich. Pluronic L62 (EO6PO34EO6) was donated by BASF. Deionized water (NANOpure Diamond UV ultrapure water system: Barnstead International), with a resistivity of 18.2 $M\Omega \cdot cm$ and surface tension of 73.8 $mN \cdot m^{-1}$ at 296 K, was used in all experiments. Glass slides (22 $mm^2$, No. 2) were obtained from Corning Labware & Equipment. Two-component epoxy (Epotek 377) was from EPO-TEK. All the other organic solvents were supplied by Fisher and were of analytical grade. $Si_3N_4$ V-shaped contact mode cantilevers with integrated pyramidal tips were purchased from Veeco Instruments (Model: NP-20). Silicon tapping-mode cantilevers were obtained from Budgetsensors, Inc. (Model: BS-Multi 75).

Figure 1:
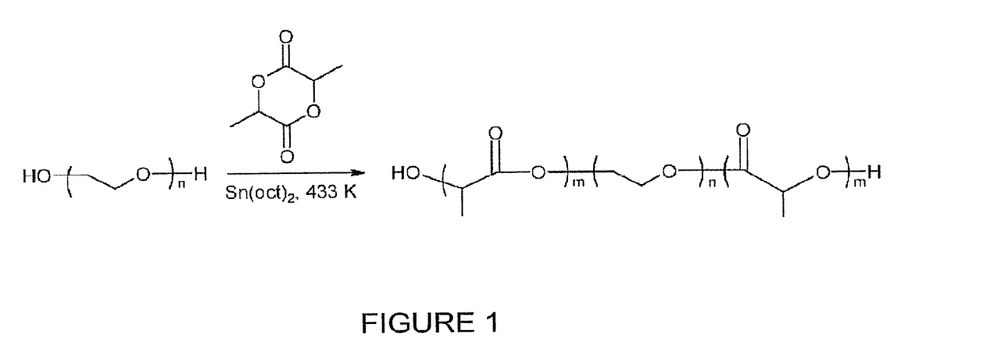
FIG. 1 illustrates the synthetic scheme for the triblock copolymers of poly(lactide)-poly(ethylene oxide)-poly(lactide) ($LA_mEO_nLA_m$).

Synthesis of the $LA_m EO_n LA_m$ Surfactants. The synthetic scheme for the triblock copolymers of poly(lactide)-poly(ethylene oxide)-poly(lactide) ($LA_m EO_n LA_m$) is illustrated in FIG. 1. An appropriate amount of PEG, dl-lactide, and stannous octoate were charged into a 25 mL round-bottomed flask under the protection of nitrogen. The reaction was carried out at 433 K under a nitrogen atmosphere for 10 h and subsequently cooled to room temperature. The products were then dissolved in methylene chloride and precipitated from ethyl ether twice, and the solvent was removed by rotary evaporation. The resulting product was finally dried under vacuum at 373 K for 12 h. 1H NMR was conducted to determine the degree of polymerization of the LA blocks, and thus the overall surfactant structure.

Preparation and Characterization of the Drug-Modified AFM Cantilever (Colloidal Probe). Single salbutamol crystals were glued onto silicon nitride contact-mode cantilevers (NP-20) with the help of an AFM (Pico LE, Molecular Imaging). In brief, the cantilever was first positioned above a tiny drop of epoxy (Epotek 377). The AFM cantilever was then slowly approached toward the epoxy. A tiny amount of it was then carefully transferred onto the AFM tip. A similar procedure was used to attach the drug particle to the AFM tip containing the epoxy. The particle-modified AFM tip was then kept at room temperature for 24 h to allow the complete curing of the epoxy. SEM images of the drug-modified cantilevers were obtained after the adhesion force measurements to verify the integrity and quality of the probe. The spring constant of the drug-modified cantilevers was determined using a module attached to the AFM and the MI Thermal K 1.02 software.

Preparation and Characterization of the Drug Crystal Substrate. Salbutamol was first dissolved in ethanol to saturation. The solution was then transferred onto a cover glass previously treated with piranha solution (7:3 v/v $H_2SO_4/H_2O_2$). The system was kept inside a sealed Petri dish. The crystallization process of salbutamol was induced by the controlled evaporation of ethanol. Optical microscopy was used to observe the crystal morphology. The surface topography of the salbutamol crystal was examined by AFM under tapping mode, with a silicon cantilever (BS-Multi 75).

Figure 2:
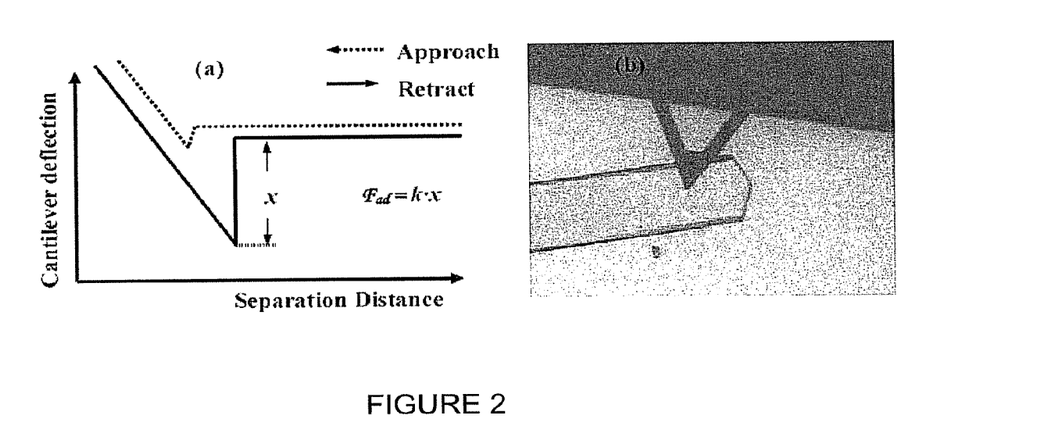
FIG. 2a shows the schematic diagram of a typical force curve obtained during CPM measurements.
FIG. 2b shows the optical image of the actual setup for the Fad measurement.

Colloidal Probe Microscopy (CPM). The force of adhesion (Fad) between the salbutamol-modified cantilever and a smooth salbutamol crystal substrate was determined by CPM, at 298 K. A fluid cell was used to perform the experiments in liquid HPFP. The procedure adopted here is similar to that used to investigate the effect of other excipients on drug-drug interactions. FIG. 2a is the schematic diagram of a typical force curve obtained during the CPM measurements. The optical image of the actual setup for the Fad measurement is shown in FIG. 2b. The Fad is determined as the product of the spring constant (k) of the drug-modified AFM cantilever and the maximum cantilever deflection (x) during the retraction stage of the force measurement; i.e., $Fad = k \cdot x$; as schematically shown in FIG. 2a.

Several contact points, randomly distributed on the crystal surfaces over a 9 μm×9 μm area, were selected for the measurements. At each contact point, 25 force-distance curves were measured. The tip was moved toward and away from the substrate in a range of 2000 nm and a sweep duration of 2 s. The histograms of the measured Fad were fit to a Gaussian distribution, from which an average Fad and deviation were obtained. The same drug probe was used throughout the measurements to guarantee a constant contact area. Great care was taken to guarantee the integrity of the drug probe. Since the solubility of salbutamol in HPFP is negligible, before each new adhesion force measurement, the drug probe and drug crystal substrate were thoroughly rinsed with HPFP, followed by an Fad test in pure HPFP. In all cases, the average variation on the adhesion force in pure HPFP was statistically insignificant, thus indicating that the integrity of the drug probe was maintained from one force measurement to the other. A second set of completely independent measurements (new probe and crystal substrate) were obtained to assess the reproducibility of the reported trend in Fad.

Characterization of the Drug Dispersion in HFA. An exact mass of micronized salbutamol particles were initially fed into pressure proof glass vials (68000318, West Pharmaceutical Services) and crimp-sealed with 50 μL metering valves (EPDM Spraymiser, 3M Inc.). Subsequently, a known amount of HFA227 was added with the help of a manual syringe pump (HiP 50-6-15) and a home-built high-pressure aerosol filler, to make a 2 mg·mL-1 drug concentration in the propellant HFA. The dispersions were then sonicated in a low-energy sonication bath (VWR, P250D, set to 180 W) for several minutes to break up large aggregates. The physical stability of the suspensions in propellant HFA was investigated by visually monitoring the dispersion as a function of time after mechanical energy input ceased. The procedure described here is similar to other reports involving the study of pMDI-based dispersions.

Results and Discussion

Surfactant Synthesis. Poly(lactide) (PLA) is being used in a wide variety of pharmaceutical and medical applications due to its low toxicity, biocompatibility, and biodegradability. To take advantage of these excellent properties, PLA has been modified with other moieties such as poly(caprolactone) (PCL) and PEG. Copolymers of LA and EO are interesting given the lower toxicity generally associated with nonionic amphiphiles and the polar nature of EO. Triblock copolymers with the general structure $LA_mEO_nLA_m$ were obtained by ring-opening polymerization of dl-lactide widi PEG as initiator and stannous octoate as catalyst. The use of PEG diol results in an ABA-type triblock copolymer. The degree of polymerization of the LA is dependent on the feed ratio of lactide over PEG and was characterized by 1H NMR. The structures of the copolymers synthesized in this work are shown in Table 1.

TABLE 1

Average Degree of Polymerization of the Lactide ($DP_{LA}$), Molecular Weight (MW) of PEG, and Overall Weight Percent of Ethylene Oxide (EO) in the Copolymers[a]

| Structure | MW PEG | EO (wt %) | $DP_{LA}$ |
| --- | --- | --- | --- |
| $LA_{107}EO_{45}LA_{107}$ | 2000 | 12 | 215 |
| $LA_{53}EO_{22}LA_{53}$ | 1000 | 12 | 107 |
| $LA_{18}EO_{14}LA_{18}$ | 600 | 19 | 36 |
| $LA_4EO_{14}LA_4$ | 600 | 51 | 8 |
| $LA_1EO_{14}LA_1$ | 600 | 81 | 2 |

[a]Subscripts indicate the average number of repeat units.

Figure 3:
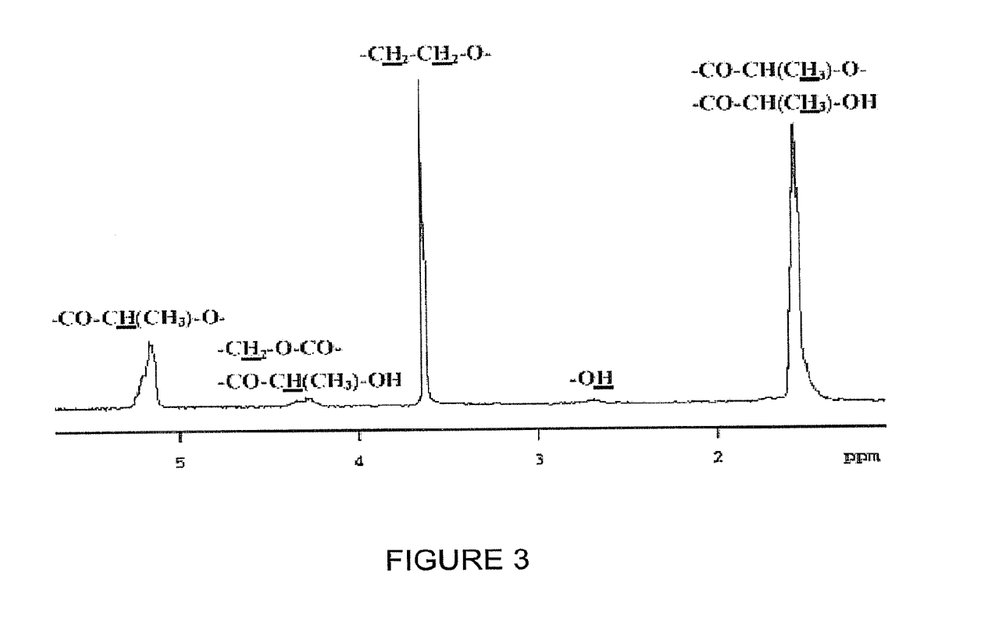
FIG. 3 shows an example of the 1H NMR spectrum of the triblock LA18EO14LA18, which was synthesized from PEG600.

The $^1H$ NMR spectrum of the triblock $LA_{18}EO_{14}LA_{18}$, which was synthesized from PEG600, is shown in FIG. 3 as an example. The degree of polymerization of the LA block was calculated from the integral intensities of —$CH_2$—$CH_2$-0- (3.6 ppm) from PEG and —CO—CH($CH_3$)—O— (1.5 ppm) from LA.

Figure 4:
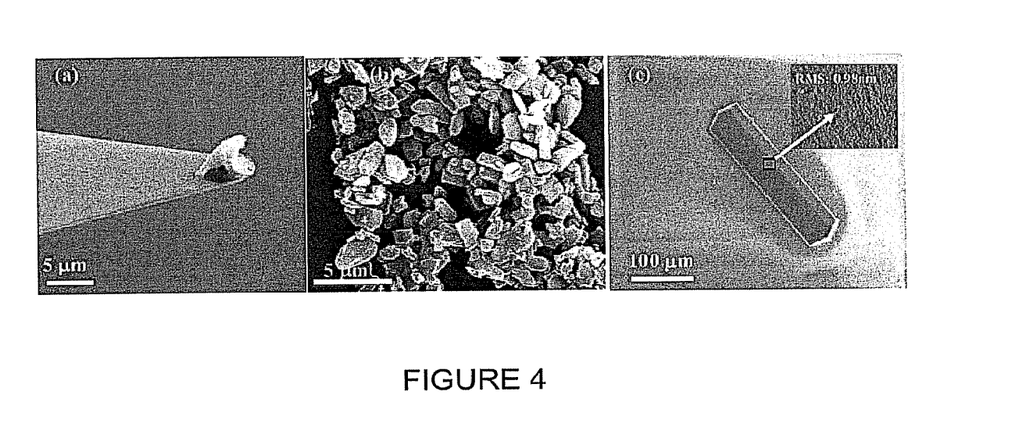
FIG. 4a is the SEM micrograph of a salbutamol-modified probe.
FIGS. 4b and 4c show a representative SEM image of the micronized salbutamol particles and the recrystallized salbutamol single crystal respectively.

Characterization of the Drug Probe and the Single-Crystal Substrate. SEM images of the drug-modified AFM cantilevers were obtained after the adhesion force (Fad) measurements. FIG. 4a is the SEM micrograph of a salbutamol-modified probe. The particle is seen to completely cover the pyramidal tip, thus acting as the first contact point during the Fad measurements. A representative SEM image of the micronized salbutamol particles and the recrystallized salbutamol single crystal are shown in FIGS. 4b and 4c, respectively. The size of the micronized particles is between 1 and 5 μm. A typical salbutamol single crystal (recrystallized from ethanol) is around 500 μm in length and 80 μm in width. The topography of the crystal surface was determined by tapping-mode AFM. The root-mean-square (rms) roughness of the drug surface over an area of 9 μm×9 μm is only 0.98 nm, indicating that the crystal surface is highly smooth, thus providing a uniform contact area for the CPM experiments. The rms of a large single crystal before and after contacting it with an HPFP+ethanol solution saturated with the drug for 20 min was determined. The absence of any significant variation agrees with the constancy of the Fad in pure HPFP determined after each experiment and suggests that the integrity of the surface is maintained.

Figure 5:
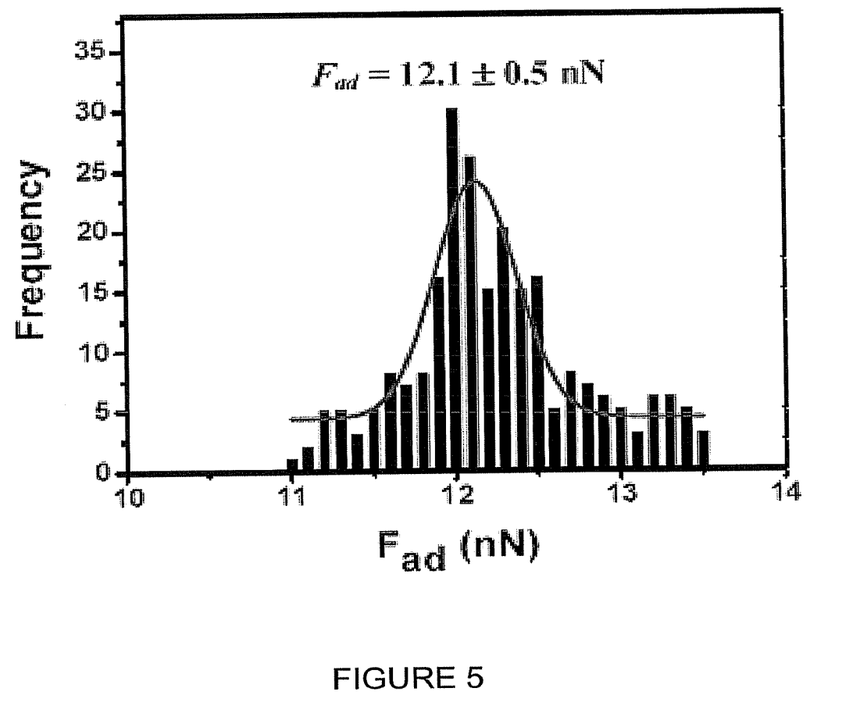
FIG. 5 shows the frequency distribution histogram of the adhesion force (Fad) between a salbutamol particle and the smooth single salbutamol crystal in pure HPFP.
Figure 6:
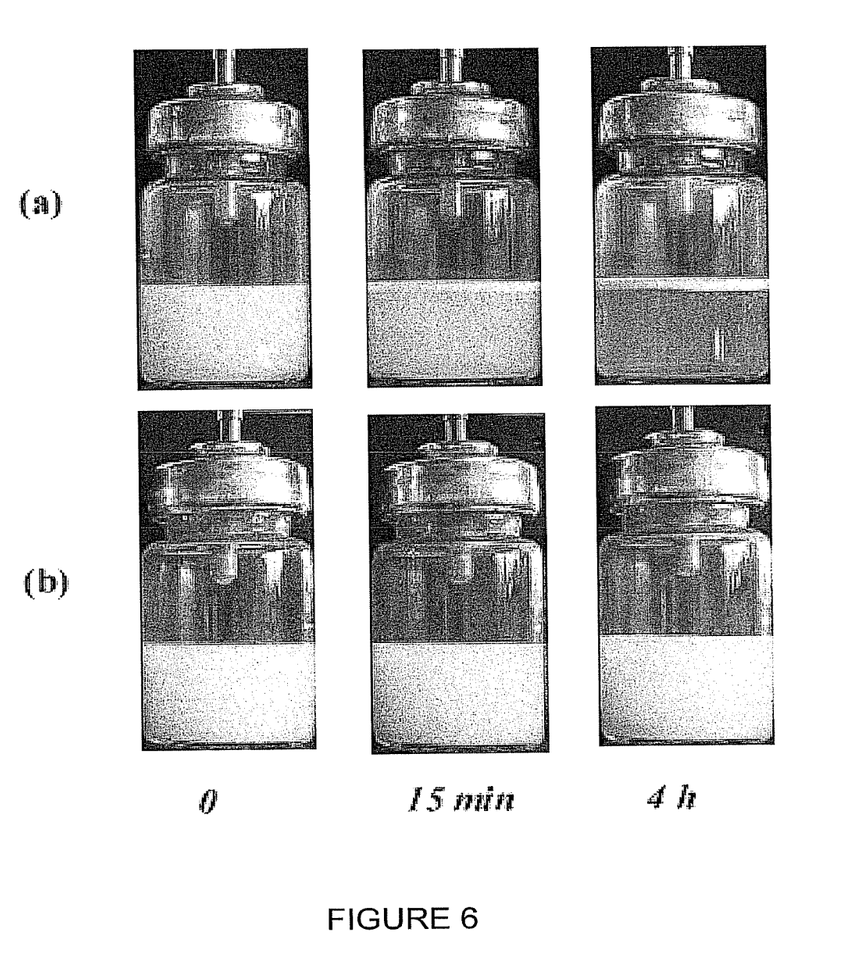
FIG. 6 shows snapshots of the suspensions as a function of the elapsed time after sonication.
Figure 7:
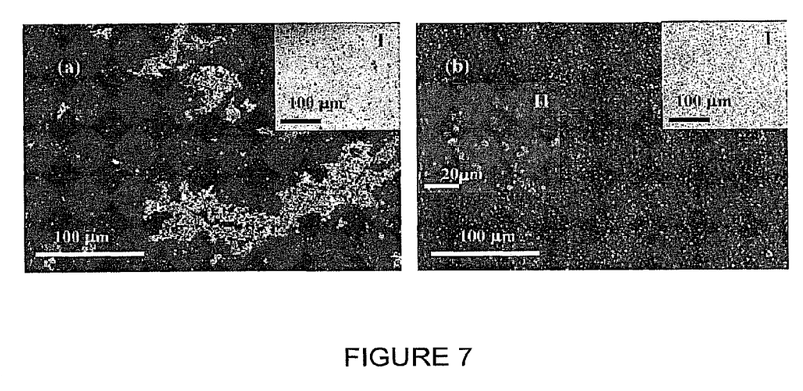
FIG. 7 shows SEM and optical images of the particles from dispersions in both pure HPFP, and from a 0.1 mM LA53EO22LA53 HPFP solution.

Colloidal Probe Microscopy. Effect of Surfactant Type and Cosolvent. The frequency distribution histogram of the adhesion force (Fad) between a salbutamol particle and the smooth single salbutamol crystal in pure HPFP is shown in FIG. 5. This is the baseline system, containing no surfactant or cosolvent. A large average adhesion force was observed in this case.

The ability of surfactants and cosolvent (ethanol) to screen the cohesive forces between a salbutamol drug crystal and a smooth single crystal was subsequently tested. The summary of the Fad results is shown in Table 2. The average Fad and standard deviation were obtained using the procedure described above. The results for two independent sets of measurements (different probe and substrate) are reported. Comparison between the two sets of experiments is limited, however, to the trends in Fad. This has to do with the fact that the absolute values of the Fad cannot be normalized to tip radius since the contact area between probes and substrate vary due to the different geometries of the drug crystals (irregular shape) being attached to the AFM probes. This is typical in such measurements. The trend in Fad in this work is shown to be consistent for both sets of experiments (probe 1 and 2). The results are discussed in terms of probe 1. It is worth noting that the type of interaction between the probe and single crystal observed during the CPM measurements is likely different from those observed in the actual suspension in the propellant HFA. This is due to the fact that drug crystals have a large variability in size, shape, and morphology. The fact that such a variability is not present in the CPM experiments is a strength of the CPM technique with regards to screening excipients for pMDIs when compared to bulk sedimentation rate experiments.

TABLE 2

Average Adhesion Force ($F_{ad}$) between the Salbutamol-Modified Probe and Smooth Salbutamol Crystal, as Determined by Colloidal Probe Microscopy (CPM) in the Presence of Surfactants and/or Cosolvents[a]

| surfactant | cosolvent | EO (wt %) | surf. conc. (mM) | $F_{ad}$ (nN) probe 1 | $F_{ad}$ (nN) probe 2 |
| --- | --- | --- | --- | --- | --- |
| None | None | | | 12.13 ± 0.50 | 8.43 ± 0.30 |
| None | Ethanol 7% (v/v) | | | 6.31 ± 0.47 | 5.01 ± 0.26 |

TABLE 2-continued

Average Adhesion Force ($F_{ad}$) between the Salbutamol-Modified
Probe and Smooth Salbutamol Crystal, as Determined by Colloidal Probe
Microscopy (CPM) in the Presence of Surfactants and/or Cosolvents[a]

| surfactant | cosolvent | EO (wt %) | surf. conc. (mM) | $F_{ad}$ (nN) probe 1 | probe 2 |
|---|---|---|---|---|---|
| Oleic acid | Ethanol 7% (v/v) | | 1.0 | 1.54 ± 0.35 | 1.64 ± 0.21 |
| $EO_6PO_{34}EO_6$ | None | 20 | 1.0 | 3.80 ± 0.41 | 2.91 ± 0.27 |
| $LA_{18}EO_{14}LA_{18}$ | None | 20 | 1.0 | 0 | 0 |

[a]Experiments were performed in liquid HPFP at 298 K.

It is interesting to observe that the introduction of cosolvent (ethanol) alone can significantly reduce the $F_{ad}$ compared to pure HPFP, indicating that the mixture of HPFP and ethanol can screen drug-drug interactions much better than pure HPFP. The presence of ethanol has two effects on the system. Ethanol is a better solvent environment for polar compounds, including salbutamol base, thus directly aiding HFA in screening the drug-drug cohesive forces.

Moreover, the solubility of oleic acid increases in the presence of ethanol. This effect is expected to further contribute to the decrease in Fad, as seen experimentally. Particle-particle interaction can be further reduced by introducing oleic acid to the HPFP/ethanol mixture, as indicated by the observed Fad of 1.54 nN. This system is similar to a commercial formulation of salbutamol sulfate in HFA134a. Although there is a significant decrease in Fad in comparison to the system with pure HPFP, the cohesive forces are not screened very effectively. Given the appreciable solubility of salbutamol in ethanol, extra care was taken to maintain the integrity of the probe during the force measurements in HPFP-ethanol and HPFP-ethanol-oleic acid mixture. These measurements were conducted at the end of the series and performed in an expeditious manner in a saturated solution of salbutamol in HPFP/ethanol mixture. The effect of another commercially available surfactant, EO6PO34EO6, on the Fad was also investigated. A significant reduction in Fad was observed, but the magnitude of the Fad was still large, and greater than the system with oleic acid and ethanol. This copolymer was chosen because it has a similar % EO in the molecule and similar overall number of PO units as in the LA18EO14LA18 surfactant synthesized in this work. The results serve, therefore, to compare the relative HFA-philicity of PO and LA.

LA18EO14LA18 at 1 mM concentration (and no cosolvent) is capable of completely screening the cohesive forces between salbutamol particles as indicated by the zero Fad. This result indicates that the chosen LA-based amphiphile has the appropriate balance to adsorb at the drug surface. It also shows that LA moiety interacts well with (is well-solvated by) the hydrofluoroalkane solvent. While the EO moiety is expected to interact with the drug through hydrogen bonds, this moiety also interacts with the dipole of HFA. The fact that both moieties of the amphiphile (EO and LA) can interact with the dispersing medium makes the identification of an optimum surfactant balance in HFA a more subtle issue when compared to traditional alkane solvents. For the same reason, PEG alone is capable of reducing (to some extent) drug-drug interactions in HPFP, as probed by CPM.

Effect of Surfactant Tail Length. The function of the LA moiety is to act as a steric barrier to prevent the strong cohesive forces between drug crystals in solution. Stabilization will be achieved when the tails are well-solvated, and long enough to prevent particles from approaching each other to distances where van der Waals attractive interactions overcome the repulsive steric forces. The number of LA repeat units is also relevant to its biodegradability, which varies with tail length. The larger the number of repeat units, the lower the rate of degradation of the LA moiety. Therefore, the effect of a series of surfactants with varying number of LA repeat units and constant number of EO groups on the Fad of salbutamol was investigated. The results are summarized in Table 3.

TABLE 3

Effect of the LA Trail Length on the Adhesion Force ($F_{ad}$) between Salbutamol-Modified Probe and Salbutamol Smooth Crystal[a]

| surfactant | $F_{ad}$ (nN) |
|---|---|
| $LA_1EO_{14}LA_1$ | 8.42 ± 0.61 |
| $LA_4EO_{14}LA_4$ | 5.87 ± 0.38 |
| $LA_{18}EO_{14}LA_{18}$ | 0 |

[a]Measurements were performed in HPFP at 298 K and 1 mM surfactant concentration.

It can be seen that the Fad is a strong function of the length/number of repeat units of the HFA-phile. Only the amphiphiles with the longest LA tails were able to completely screen the cohesive forces between the salbutamol crystals. In spite of the fact that the surface concentration of the copolymers (on the drug crystals) has not been determined, it is safe to assume that the observed Fad results reflect a combination of both surfactant balance and steric barrier provided by the LA moiety. While an appropriate balance is required to drive the amphiphile to the interface between the drug and the HFA solvent, a long enough LA tail is required to screen the interaction between the drug particle and the smooth drug crystal.

Effect of Surfactant Concentration. The effect of the concentration of the amphiphile on drug-drug interaction was also evaluated. Surfactant concentration is an important variable in commercial formulations. Clearly, the amount of non-active excipient is to be minimized to reduce potential toxicity effects and its impact on the physical properties of the propellant-excipient mixture. The results for Fad between the drug-modified cantilever and the drug crystal in HPFP in the presence of LA107EO45LA107 and LA53EO22LA53 at different concentrations are summarized in Table 4. The surfactants have different block lengths, but the same % EO in the molecule. The partition to the drug interface is expected to be somewhat similar.

TABLE 4

Effect of Surfactant Concentration and Molecular
Weight on the Adhesion Force ($F_{ad}$) between
Salbutamol-Modified AFM Probe and Smooth Salbutamol
Crystal in HPFP at 298 K

| surfactant | EO (wt %) | surf. conc. (mM) | $F_{ad}$ (nN) |
|---|---|---|---|
| $LA_{107}EO_{45}LA_{107}$ | 12 | 0.5 | 0 |
| | | 0.1 | 0 |
| | | 0.05 | 0.27 ± 0.14 |
| $LA_{53}EO_{22}LA_{53}$ | 12 | 0.5 | 0 |
| | | 0.1 | 0 |
| | | 0.05 | 1.09 ± 0.35 |

The results indicate that the minimum concentration below which the Fad becomes attractive is independent of the overall MW of the amphiphile, at least for the range investigated. However, the magnitude of the force is greater (more attractive) for the amphiphile with the lower MW. There are many confounding effects that may influence the magnitude of the force, including the fact that the weight concentration is different and that the critical aggregation concentration (cac) and total adsorbed amount for those amphiphiles on the drug crystal and substrate are not known.

Physical Stability of the Formulations. The physical stability of a 2 mg·mL-1 salbutamol suspension in pure HFA227 and in 0.1 mM LA53EO22LA53 solution in HFA227 was investigated, and the results correlated with the Fad obtained by CPM. Snapshots of the suspensions as a function of the elapsed time after sonication are shown in FIG. 6. While low MW oligolactic acid is highly soluble in HFA134a,11 the solubility of the $LA_mEO_nLA_m$ copolymers was found to be fairly limited. Therefore, comparative stability studies were not performed in HFA134a.

The stability of the dispersion in the LA53EO22LA53 formulation is, as expected, superior compared to that in pure HFA227. In pure HFA227, creaming of the drug particles started immediately after mechanical input to the system ceased, as shown in FIG. 6*a*. The formulation with the LA-based amphiphile turned out to be significantly more stable, with creaming rates on the order of hours. The physical stability of the salbutamol base in HFA227 in the presence of ethanol (solution not saturated with the drug) cannot be directly assessed because crystal formation takes place several minutes after the formulation is prepared. The physical stability of the drug suspension in HPFP was observed to be similar to that in HFA227. These results are in direct agreement with the Fad obtained by CPM; i.e., amphiphiles capable of decreasing the Fad (screening cohesive forces) are capable of imparting physical stability to the system.

The particles dispersed in HPFP were examined soon after sonication was stopped. SEM and optical images of the particles from dispersions in both pure HPFP, and from a 0.1 mM LA53EO22LA53 HPFP solution, are shown in FIG. 7.

The images demonstrate that salbutamol particles in pure HPFP tend to reaggregate soon after being dispersed (FIG. 7*a*). On the other hand, the micrograph in FIG. 7*b* shows that the particles from the dispersion in the 0.1 mM LA53EO22LA53 HPFP solution remain homogeneously dispersed. While part of the aggregation seen in the SEM image shown in FIG. 7*a* (pure HPFP) may have been induced during solvent evaporation, the optical image (inset of FIG. 7*a*) clearly indicates the presence of flocculated domains in pure HPFP. The same does not happen for the LA-based system.

The ability of biocompatible and biodegradable lactide (LA)-based amphiphiles to screen the cohesive forces of a model drug (salbutamol base) in a mimicking hydrofluoroalkane (HFA) propellant, HPFP were assessed. Adhesion force (Fad) results from colloidal probe microscopy (CPM) were obtained for a series of surfactants with varying MW, length of the ethylene oxide (EO) block, and hydrophilic-to-HFA-philic balance (HFB, LA/E0 ratio). While cohesive forces between salbutamol crystals can be somewhat suppressed upon the addition of ethanol and oleic acid to HPFP, the forces are only partially screened. In sharp contrast, the LA-based triblock copolymers ($LA_mEO_nLA_m$) are capable of reducing the cohesive forces down to zero, even in the absence of cosolvent. The results indicate that the LA moiety can be well-solvated by HPFP and is thus able to provide a steric barrier to flocculation. The physical stability of the formulations in HPFP is in excellent agreement with the Fad results from CPM. Physical instability due to flocculation is observed for systems with large Fad, while long-term stability is observed for systems with low (zero) Fad. Most importantly, the results in the propellant HFA227 were seen to correlate well with the Fad and physical stability results in HPFP. CPM results also indicated that the overall MW, surfactant concentration, size of the EO group, and HFB all affect the cohesive forces. These results serve to illustrate the sensitivity of the approach, and the potential of this technique to design novel excipients for HFA-based pMD formulations. The applicability of LA-based amphiphiles might be extended to other suspension-based formulations provided a suitable headgroup is found.

The ability of biodegradable and biocompatible lactide-based nonionic amphiphiles to stabilize a model drug (salbutamol base) dispersion in hydrofluoroalkane (HFA) propellant was evaluated. A series of triblock copolymers of the type poly(lactide)-poly(ethylene glycol)-poly(lactide) ($LA_mEO_n$-$LA_m$) with varying molecular weight (MW) and % EO were synthesized. The cohesive forces between drug particles in liquid HFA in the presence of the amphiphiles were quantitatively determined by colloidal probe microscopy (CPM). The effect of cosolvent, oleic acid, and a nonionic triblock copolymer with the propylene oxide moiety as the HFA-phile was also investigated. CPM results show that the overall concentration, MW, surfactant tail (LA) length, and the ratio between the stabilizing LA moiety and the anchor EO group have a great impact on the drug cohesive forces. The CPM results in liquid HFA were correlated to the bulk physical stability of the drug suspensions in the propellant 1,1,1,2,3,3,3-heptafluoropropane (HFA227). The dispersions in HFA227 were significantly improved in the presence of $LA_mEO_nLA_m$, correlating well with the low cohesive forces determined by CPM.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

REFERENCES (1) Bell, J.; Newman, S., *Expert Opin. Drug Delivery.* 2007, 4, 215-234.
(2) Courtier, H. M.; Butz, N.; Vandamme, T. F., *Crit. Rev. Ther. Drug Carrier Syst.* 2002, 19, 425-498.
(3) Rogueda, P., *Expert Opin. Drug Deliv.* 2005, 2, 625-638.
(4) *Montreal protocol on substance that deplete the ozone layer* 261LM 1541 1987.
(5) McDonald, K. J.; Martin, G. P., *Int. J. Pharm.* 2000, 201, 89-107.
(6) Byron, P. R.; Miller, N. C.; Blondino, F. E., *Respir, Drug Delivery* 1994, 231-242.
(7) Byron, P. R.; Patton, J. S., *J. Aerosol Med.* 1994, 7, 49-75.
(8) Vervaet, C.; Byron, P. R., *Int. J. Pharm.* 1999, 186, 13-30.
(9) Tzou, T.-Z.; Pachuta, R. R.; Coy, R. B.; Schultz, R. K., *J. Pharm. Sci.* 1997, 86, 1352-1357
(10) Fink, J. B., *Respir. Care* 2000, 45, 623-635.
(11) Stefely, J. S.; Duan; D. C.; Myrdal, P. B.; Ross, D. L.; Schultz, D. W.; Leach, C. L., *Respir. Drug Delivery VII* 2000, 83-90.
(12) Traini, D.; Young, P. M.; Rogueda, P.; Price, R., *Int. J. Pharm.* 2006, 320, 58-63.
(13) Wu, L.; Peguin, R. P. S.; Selvam, P.; Chokshi, U.; da Rocha, S. R. P., *Inhalation Aerosols: Physical and Biological Basis for Therapy,* 3rd ed.; Hickey, A. J., Ed.; Informa Healthcare: New York, 2007; pp 373-397.
(14) Wu, L.; Peguin, R. P. S.; da Roche, S. R. P., *J. Phys. Chem. B* 2007, 111, 8096-8104.
(15) Ridder, K. B.; Davies-Cutting, C. J.; Kellaway, I. W., *Int J. Pharm.* 2005, 295, 57-65.
(16) Ralston, J.; Larson, I; Rutland, M. W.; Feiler, A. A.; Kleijn, M., *Pure Appl. Chem.* 2005, 77, 2149-2170.
(17) Ducker, W. A.; Senden, T., *J. Langmuir* 1992, 8, 1831-1836.
(18) Butt, H. J.; Cappella, B.; Kappl, M., *Surf. Sci. Rep.* 2005, 59, 1-152.
(19) Sakai, K.; Yoshimura, T.; Esumi, K., *Langmuir* 2003, 19, 1203-1208.
(20) Sakai, K.; Yoshimura, T.; Esumi, K., *Langmuir* 2002, 18, 3993-3998.
(21) Rutland, M. W.; Senden, T. J., *Langmuir* 1993, 9, 412-418.
(22) Biggs, S.; Proud, A. D., *Langmuir* 1997, 13, 7202-7210.
(23) Muir, I.; Meagher, L.; Gee, M., *Langmuir* 2001, 17, 4932-4939.
(24) McNamee, C. E.; Matsumoto, M.; Hartley, P. G.; Mulvaney, P.; Tsujii, Y.; Nakahara, M., *Langmuir* 2001, 17, 6220-6227.
(25) Sakai, K.; Torigoe, K.; Esumi, K., *Langmuir* 2001, 17, 4973-4979.
(26) Braithwaite, G. J. C.; Howe, A.; Luckham, P. F., *Langmuir* 1996, 12, 4224-4237.
(27) Bremmell, K. E.; Jameson, G. J.; Biggs, S., *Colloids Surf. A* 1998, 139, 199-211.
(28) Bremmell, K. E.; Jameson, G. J.; Biggs, S., *Colloids Surf. A* 1999, 155, 1-10.
(29) Telko, M. J.; Hickey, A. J., *Respir. Care* 2005, 50, 1209-27.
(30) Young, P. M.; Price, R.; Tobyn, M. J.; Buttrum, M.; Dey, F., *J. Pharm. Sci.* 2004, 93, 753-761.
(31) Price, R.; Young, P. M.; Edge, S.; Staniforth, J. N., *Int, J. Pharm.* 2002, 246, 47-59.
(32) Begat, P.; Morton, D. A. V.; Staniforth, J. N.; Price, R., *Pharm. Res.* 2004, 21, 1591-1597.
(33) Ashayer, R.; Luckham, P. F.; Manimaaran, S.; Rogueda, P., *Eur. J. Pharm. Sci.* 2004, 21, 533-543.

(34) Traini, D.; Rogueda, P.; Young, P. M.; Price, R., *Pharm. Res.* 2005, 22, 816-825.
(35) Young, P. M.; Price, R.; Lewis, D.; Edge, S.; Traini, D., *J. Colloid Interface Sci.* 2003, 262, 298-302.
(36) Peguin, R. P. S.; Wu, L.; da Rocha, S. R. P., *Langmuir* 1007, 23, 8291-8294.
(37) Hagan, S. A. D., S. E.; Garnett, M. C.; Davies, M. C.; Ilium, L.; Davis, S. S., *Proc. Ins. Symp. Controlled Release Bioact. Mater.* 1995, 22nd, 194-195.
(38) Luu, Y. K.; Kim, K.; Hsiao, B. S.; Chu, B.; Hadjiargyrou, M., *J. Controlled Release* 2003, 89, 341-353.
(39) Riley, T.; Govender, T.; Stolnik, S.; Xiong, C. D.; Garnett, M. C.; Ilium, L.; Davis, S. S., *Colloids Surf. B* 1999, 16, 147-159.
(40) Yuancai, D.; Si-Shen, F. S.-S. *Biomaterials* 2004, 25, 2843-2849.
(41) Vila, A.; Sanchez, A.; Evora, C.; Soriano, I.; Vila Jato, J. L.; Alonso, M. J., *J. Aerosol Med.* 2004, 17, 174-185.
(42) Rogueda, P. G. A., *Drug Dev. Ind. Pharm* 2003, 29, 39-49.
(43) Mohammadi-Rovshandeh, J.; Farnia, S. M. F.; Sarbolouki, M. N., *J. Appl. Polym. Sci.* 1999, 74, 2004-7009.
(44) Jones, S. A.; Martin, G. P.; Brown, M. B., *Int. J. Pharm.* 2005, 302, 154-165.
(45) Jones, S. A.; Martin, G. P.; Brown, M. B., *J. Controlled Release* 2006, 115, 1-8.
(46) Jalil., R. U., *Drug Dev. Ind. Pharm.* 1990, 16, 2353-67.
(47) Okada, H.; Yamamoto, M.; Heya, T.; Inoue, Y. K.; Shigeru; Ogawa, Y.; Toguchi, H., *J. Controlled Release* 1994, 28, 121-9.
(48) Huang, M.-H.; Coudane, J.; Li, S.; Vert, M. J., *Polym. Sci.*, A 2005, 43, 4196-4205.
(49) Young, P. M.; Price, R.; Tobyn, M. J.; Buttrum, M.; Dey, F., *J. Pharm. Sci.* 2003, 92, 815-822.
(50) Williams, R. O., Repka, M. A.; Barron, M. K., *Eur. J. Pharm. Biopharm.* 1999, 48, 131-140.
(51) Pepsin, R. P. S.; Selvam, P.; da Rocha, S. R. P., *Langmuir* 2006, 22, 8826-8830.
(52) Selvam, P.; Peguin, R. P. S.; Chokshi, U.; da Rocha, S. R. P., *Langmuir* 2006, 22, 8675-8683.
(53) Heller, W.; Pugh, T. L., *J. Polym. Sci.* 1960, 47, 203-217.
(54) Stefely, J. S.; Schultz, D. W.; Schallinger, L E.; Perman, C. A.; Leach, C. L.; Duan, D. C., U.S. Pat. No. 6,126,919, 2000.

What is claimed is:

1. A hydrofluoroalkane (HFA)-based formulation for a pressurized metered-dose inhaler comprising a surfactant comprising a triblock copolymer of the formula:

$LA_mEO_nLA_m$ wherein LA is lactide and EO is ethylene oxide; and
wherein m is 1 and n is 14;
m is 4 and n is 14;
m is 18 and n is 14;
m is 53 and n is 22; or
m is 107 and n is 45
and wherein 1, 4, 18, 53 and 107 represent the average number of repeat units for m and 14, 22 and 45 represent the average number of repeat units for n.

2. The formulation of claim 1 wherein said formulation has no co-solvent or co-surfactant.

3. The HFA based formulation of claim 1 comprising heptafluoropropane.

4. The formulation of claim 1 wherein said surfactant is at a concentration of 0.05 mM to about 1 mM.

5. The formulation of claim 1 wherein the ratio of the value of m to the value of n is 0.07, 0.3, 1.3, or 2.4.

6. A HFA-based formulation for a pressurized metered-dose inhaler comprising a surfactant comprising an ABA triblock copolymer with lactide terminal blocks and an ethylene oxide central block wherein the weight percent of ethylene oxide in the triblock copolymer is 12%, 19%, 20%, 51%, or 81%.

7. The formulation of claim 6 wherein said formulation has no co-solvent or co-surfactant.

8. The formulation of claim 6 comprising heptafluoropropane.

9. The formulation of claim 6 wherein said surfactant is at a concentration of 0.05 mM to about 1 mM.

10. A HFA-based formulation for a pressurized metered-dose inhaler comprising a surfactant comprising a triblock copolymer of the formula:

$LA_mEO_nLA_m$ wherein LA is lactide and EO is ethylene oxide; and
wherein the ratio of the value of m to the value of n is 0.07, 0.3, 1.3, or 2.4.

11. The formulation of claim 10 wherein said formulation has no co-solvent or co-surfactant.

12. The HFA-based formulation of claim 10 comprising heptafluoropropane.

13. The formulation of claim 10 wherein said surfactant is at a concentration of 0.05 mM to about 1 mM.

* * * * *